United States Patent [19]

Tachibana et al.

[11] Patent Number: 4,551,273
[45] Date of Patent: Nov. 5, 1985

[54] ANALGESIC PEPTIDE AND PROCESS FOR THE PREPARATION THEREOF

[75] Inventors: Shinro Tachibana, Kashiwa; Shizuko Ohya, Ushikumachi; Yoshihiro Arakawa, Sakuramura; Takahiro Nakazawa, Fujishiromachi; Takeru Kaneko, Yatabemachi; Masuhiro Ikeda, Toyosatomachi; Kiyomi Yamatsu, Kamakura, all of Japan

[73] Assignee: Eisai Co., Ltd., Tokyo, Japan

[21] Appl. No.: 575,804

[22] Filed: Jan. 31, 1984

[30] Foreign Application Priority Data

Feb. 1, 1983 [JP] Japan .................................. 58-13785

[51] Int. Cl.$^4$ ............................................ C07C 103/52
[52] U.S. Cl. ........................ 260/112.5 E; 260/112.5 R
[58] Field of Search ................... 260/112.5 R, 112.5 E

[56] References Cited

U.S. PATENT DOCUMENTS 4,218,474  8/1980  Barnish et al. ...................... 424/177
4,396,606  8/1983  Goldstein ...................... 260/112.5 E
4,416,820  11/1983  Fukuda et al. ............... 260/112.5 R
4,462,941  7/1984  Lee et al. ...................... 260/112.5 R

OTHER PUBLICATIONS

Tachibana et al., *Nature*, vol. 295, Jan. 28, 1982, pp. 339-340.
Huidobro-Toro, *European Journal of Pharmacology*, vol. 72, 1981, pp. 265-266.
Merrifield, *JACS*, vol. 85, 1963, pp. 2149-2154.

*Primary Examiner*—Delbert R. Phillips
*Assistant Examiner*—F. T. Moezie
*Attorney, Agent, or Firm*—Flynn, Thiel, Boutell & Tanis

[57] ABSTRACT

A novel peptide having the primary structure: N-Me-Tyr-Gly-Gly-Phe-Leu-Arg-Arg-D.Ile-Arg-Pro-Lys-D.Leu-Lys-Trp-NH$_2$ (in which D.Ile and D.Leu represent a D-Ile and a D-Leu residue respectively, other abbreviations of amino acids represent each an L-amino acid residue and Me represents a methyl group), which exhibits a remarkable analgesic effect when administered peripherally. A process for the preparation thereof by a solid phase method is also disclosed.

1 Claim, No Drawings

ANALGESIC PEPTIDE AND PROCESS FOR THE PREPARATION THEREOF

BACKGROUND OF THE INVENTION

This invention relates to a novel analgesic peptide and a process for the preparation thereof.

Studies of the analgesic mechanism of morphine have suggested that there might be so-called endogenous morphine-like substances which control sensations including algesia and mental operations in vivo. In fact, the presence of a series of opioid peptides such as enkephalin or endorphin has been identified in the brain. There are two types of pentapeptide enkephalins, namely methionine enkephalin and leucine enkephalin, having different physiological effects from one another. Furthermore, endorphin has been known to have analogs such as α, β, γ, δ, etc. Among them, β-endorphin consisting of 31 amino acids seems to exhibit the highest analgesic effect. The following literature references give summaries of knowledge heretofore acquired about endorphin:

A. Beaumont, J. Hughes: Ann. Rev. Pharmacol. Toxicol., 19, 245 (1979); T. Oyama: Diagnosis and Treatment, 68, 825 (1980); and Protein, Nucleic acid and Enzyme, 26, No. 2 (1981); Special Number featuring Articles on Opioid Peptides.

Recent studies have suggested that the endogenous morphine-like substances might occur not only in the brain but also in other regions in vivo. A few peptides regarded as precursors of enkephalin were actually isolated from adrenal medulla. It has also been suggested that some morphine-like substances might occur in the intestinal tract by using immunological methods such as fluorescent antibody method or radioimmunoassay, or bioassay in vitro. Under these circumstances, some of the present inventors inadvertently found a substance having a morphine-like activity during the purification of a bathoactive intestinal peptide obtained from pig duodenum. Further purification and analysis of the corresponding substance showed that it was a novel peptide having the following primary structure which exhibited a morphine-like activity several hundred times as high as morphine:

Tyr-Gly-Gly-Phe-Leu-Arg-Arg-Ile-Arg-Pro-Lys-Leu-Lys-Trp-Asp-Asp-Gln.

Consequently the obtained novel peptide was an opioid peptide, which proved the presence of opioid peptides in the intestinal tract. Further investigations of pharmacological effects of this peptide which had been synthesized separately showed that it exhibited a high analgesic effect when administered intraventricularly and combined selectively with a kappa-receptor belonging to a subclass of an opiate receptor. That is to say, said peptide exhibits an analgesic effect by combining with a receptor different from the μ-receptor which combines with morphine, which suggests that it may be an analgesic with no addiction. The following literature references give information about said peptide:

S. Tachibana et al. Nature, 295, 339 (1982); Japanese Patent Application No. 112950/1981, now Japanese Patent Publication (Unexamined) No. 15946/83, corresponding to U.S. Pat. No. 4 481 138; and J. P. Huidobro-Toro et al., Eur. J. Pharmacol., 72. 265 (1981).

Peptide will rapidly decompose in vivo in general, and undecomposed residue thereof can hardly pass through the blood-brain barrier. Therefore, when an opioid peptide is administered directly to a peripheral region (e.g. intravenously), the resulting analgesic effect is derived from a very small part of the dose. Consequently it must be very effective for improving the usefulness of an opioid peptide, if possible, to formulate it to minimize the decomposition in vivo. This is true also in the case of the above-mentioned, peptide found by some of the present inventors.

SUMMARY OF THE INVENTION

From such a viewpoint, the inventors have formulated a novel peptide having the following primary structure, by reference to the above-mentioned peptide, which will hereinafter be called the prototype peptide of the present invention:

N-Me-Tyr-Gly-Gly-Phe-Leu-Arg-Arg-D.Ile-Arg-Pro-Lys-D.Leu-Lys-Trp-NH$_2$ in which D.Ile and D.Leu represent a D-Ile and a D-Leu residue respectively, other abbreviations of amino acids represent each an L-amino acid residue and Me represents a methyl group.

First we selected a fragment of the following primary structure from the prototype peptide:

Tyr-Gly-Gly-Phe-Leu-Arg-Arg-Ile-Arg-Pro-Lys-Leu-Lys-Trp.

Then the N-terminal amino group of the above-mentioned tetradecapeptide was monomethylated in order to depress the hydrolysis of the N-terminal amino group by aminopeptidase. The C-terminal amino acid of the above-mentioned tetradecapeptide was amidated in order to depress the hydrolysis by carboxypeptidase. Furthermore, in order to inhibit the hydrolysis by trypsin-like endopeptidase, the relevant amino acids of the above-mentioned tetradecapeptide were converted into D-forms thereof (more particularly, the eighth isoleucine and the twelfth leucine from the N-terminal were converted into D-isoleucine and D-leucine respectively).

The inventors have prepared the peptide of the above-mentioned primary structure and examined the pharmacological effect thereof. Consequently it has been found that said peptide exhibits not only a morphine-like activity but a remarkable analgesic effect which is also observed by intravenous administration as expected and found to be higher than that of morphine on a molar basis, resulting in the perfection of the present invention. That is to say, an object of the present invention is to provide a novel peptide which exhibits a higher analgesic effect than that of morphine when administered peripherally. In order to accomplish the foregoing object, the peptide of the above-mentioned primary structure and a process for the preparation thereof will be disclosed in the invention.

DETAILED DESCRIPTION OF PREFERRED EMBODIMENTS

The compound of the present invention is a tetradecapeptide having the following primary structure:

N-Me-Tyr-Gly-Gly-Phe-Leu-Arg-Arg-D.Ile-Arg-Pro-Lys-D.Leu-Lys-Trp-NH$_2$ in which D.Ile and D.Leu represent a D-Ile and a D-Leu residue respectively, other abbreviations of amino acids represent each an L-amino acid residue and Me represents a methyl group.

This primary structure can be determined by summarizing the results obtained from: analysis of the amino acid composition of the compound of the present invention; identification of the N-terminal amino acid by dansylation; and analysis of the amino acid composition, identification of the N-terminal amino acid thereof and determination of the amino acid sequence by Edman degradation of a fragment obtained by trypsin-decomposition of the compound of the present invention.

Physicochemical properties, particularly those obtained from TLC, high-voltage paper electrophoresis and HPLC, of the compound of the present invention will be shown in Example 1 described hereinafter.

The compound of the present invention may be synthesized by a well-known solid phase or liquid phase method. For example, it may be synthesized according to a solid phase method which has been called in general a Merrifield method (R. B. Merrifield, JACS, 85, 2149 (1963)) by using Synthesizer Model 990 B (a product of Beckman Co., Ltd.) as follows.

Tryptophan protected at the amino group with a tertbutoxycarbonyl group (BOC) is bonded through an amide bond with a styrene resin carrier. After eliminating the protecting group, it is condensed with lysine which has been previously protected at the alpha-amino group with, for example, a BOC and at the side-chain amino group with an o-chlorobenzyloxycarbonyl group to form a peptide bond. In this reaction, three equivalents of the lysine protected at the amino groups are used with a mixture of dicyclohexylcarbodiimide (DCC) and 1-hydroxybenzotriazole (HOBT) as condensing agent. The end point of the reaction is detected by ninhydrin reaction. Thus, amino acids protected at the N-terminal and, if necessary, at a functional group in the side chain might be condensed in series according to the amino acid sequence of the primary structure of the compound of the present invention to thereby afford finally the compound of the present invention protected at the N-terminal and functional groups. Finally, it is treated with hydrogen fluoride to eliminate the protecting groups and the resin, with the addition of anisole to suppress side reactions. The crude product obtained by removing hydrogen fluoride may be purified by counter-current distribution chromatography followed by ion-exchange chromatography with CM-cellulose. Then it may be subjected to high-performance liquid chromatography to ascertain the purity and purified, if necessary, by partition chromatography with Sephadex and preparative high-performance liquid chromatography to obtain a pure compound of the present invention. The purity and structure of the compound of the present invention may be identified by TLC, high-performance liquid chromatography, high-voltage paper electrophoresis and amino acid analysis following the hydrolysis with acid.

The following experimental examples show that the compound of the present invention may be a useful substance having an analgesic effect.

Experimental Example 1

(1) Sample

A compound of the present invention prepared by the method as will be described below in Example 1 was used as a sample. Morphine was used as a control.

(2) Method

The following two methods (A) and (B) were employed.

(A) Assay with guinea pig longitudinal muscle of ileum

This assay was carried out according to the method reported by H. W. Kosterlitz et al. A mature guinea pig was sacrificed by cutting its jugular and subjected to an abdominal operation to take out its ileum as a piece of 40 to 50 cm in length from a region 15 to 20 cm apart from the ileocecal region. Then it was immediately introduced into Ringer's solution and cut into 10 cm portions. The longitudinal muscle was peeled off from each piece by using a scalpel and an applicator, wound with a string and suspended in an isothermal glass cell of 6 ml in volume. Subsequently it was stimulated electrically (0.1 Hz, 0.5 ms, 80–90 V) with platinum electrodes fitted at the upper and lower sides of the cell to record the resulting contractions through a transducer. The morphine-like activity of the sample was determined by the inhibitory degree of contraction which depended on the amount of the sample introduced into the cell.

The literature reference about this method is as follows:

H. W. Kosterlitz, A. A. Waterfield: Annu. Rev. Pharmacol., 15, 29 (1975).

(B) Assay with mouse vas deferens

This assay was carried out according to the method reported by Hughes et al. A mature male mouse was decapitated and phlebotomized. Then it was immediately subjected to an abdominal operation to take out its right and left vas deferens. Sperm clogged in the ducts was forced out with a pincette in Ringer's solution and both ends of the two ducts were united with a string to form a ring. Then it was stimulated electrically (0.1 Hz, 1 ms, 90 V) in the same manner as described in (A). The morphine-like activity of the sample was determined by the inhibitory degree of contraction, similarly to the case of the guinea pig longitudinal muscle of ileum.

The literature reference about this method is as follows:

Hughes H. W., Kosterlitz H. W., Leslie F. M.: Br. J. Pharmacol., 53, 371 (1975).

In addition, since the titer of the morphine-like activity is expressed in $IC_{50}$ (nmol) which represents the concentration of a sample required to decrease contraction resulting from an electrical stimulation to 50%, the values of $IC_{50}$ were also determined in methods (A) and (B).

(3) Results

Results are shown in Table 1.

TABLE 1

| Sample | Method (A) | Method (B) |
| --- | --- | --- |
| Morphine | 94 ± 36 | 1068 ± 489 |
| Compound of the present invention | 0.35 ± 0.20 | 1.1 ± 0.4 |

The values in the table represent $IC_{50}$ (nmol).

Table 1 suggests that the compound of the present invention would inhibit the contraction of the guinea pig longitudinal muscle of ileum caused by an electric stimulation approximately 270-fold as highly as morphine. It also suggests that the compound of the present invention would inhibit the contraction of the mouse vas deferens caused by an electric stimulation approximately 970-fold as highly as morphine.

Experimental Example 2

(1) Sample

The compound of the present invention prepared by the method as described in Example 1 was used as a sample. Morphine was used as a control.

(2) Method

The following two methods (A) and (B) were employed to examine the analgesic effects of the sample resulting from intravenous or intraventricular administration.

The sample and control were injected to the tail vein in the case of intravenous administration and to the side cerebral ventricle in the case of intraventricular administration according to a method reported by Haley and McCormick(1).

(A) Acetic acid writhing assay 0.1 ml/10 g of a 0.7% solution of acetic acid was administered to a ddY male mouse of 20 to 26 g in body weight by an intraabdominal injection to examine the inhibiting effect on writhing syndrome which was mainly observed as a stretching of the hind legs as an indication of the analgesic effect. Acetic acid was administered intraabdominally five min after the intraventricular administration and 10 min after the intravenous administration of the sample. Then the resulting writhing syndromes were counted for 15 min.

(B) Tail pinch assay

The analgesic effect was observed with the elapse of time by observing the inhibiting effect on biting response(2) (false pain response) induced by pinching the mouse tail with an arterial clamp (300 g) as an indication.

Response time had been previously determined by a pressure stimulation to select the mice which had responded within 3 sec for the experiment. According to a method reported by Takagi et al.(3), the degree of pain was scored in the following three stages depending on the response time; 0 (shorter than four sec), 1 (four to eight sec), 2 (longer than eight sec). The analgesic effect was calculated by the following equation:

$$\text{analgesic effect (\%)} = \frac{\Sigma(\text{each score})}{2 \times \text{number of mice}} \times 100$$

In addition, the efficient doses for 50% analgesic ($ED_{50}$) were calculated by Litchfield & Wilcoxon's method(4) in the both tests of (A) and (B).

The literature references about this method are as follows:

(1) T. J. Haley and W. G. McCormick: Brit. J. Pharmacol., 12, 12 (1957),
(2) F. Haffner: Deut. Med. Wochschr., 55, 731 (1929),
(3) H. Takagi et al.: Jap. Pharmacol., 16, 287 (1966),
(4) J. T. Jr. Litchfield and F. Wilcoxon: J. Pharmacol. Exp. Ther., 96, 99 (1949).

(3) Results

Results are shown in Table 2.

TABLE 2

| Method | (A) | | (B) |
|---|---|---|---|
| Administration | intraventricular | intravenous | intraventricular |
| Morphine | 0.63 | 32 | 0.24 |
| Compound of the present invention | 0.017 | 3.4 | 0.017 |

The values in the table represent $ED_{50}$ (nmol/head).

Table 2 shows that the compound of the present invention would also exhibit an analgesic effect when administered intravenously as expected and its effect is higher than that of morphine on a molar basis.

To further illustrate the present invention, the following examples are given.

EXAMPLE 1

5 g of benzhydrylamine resin containing 2 mmol/5 g of amino group was introduced into a reactor of an automatic peptide synthesizer (Model 990 B; a product of Beckman Co., Ltd.). Then 1.82 g (6 mmol) of BOC-Trp dissolved in a mixture of 10 ml of DMF and 50 ml of dichloromethane was added. Subsequently 12 ml (6 mmol) of a 0.5M DCC/dichloromethane solution was added and the mixture was allowed to condense for five hours at room temperature. Then the resin was separated by filtration and the following procedures were carried out subsequently:

(1) washing with three 100 ml portions of dichloromethane;
(2) pre-washing with 100 ml of a dichloromethane solution of 33% TFA and 1% indole;
(3) eliminating the protecting group with 100 ml of a dichloromethane solution of 33% TFA and 1% indole;
(4) washing with 100 ml of dichloromethane;
(5) washing with 100 ml of ethyl alcohol;
(6) washing with two 100 ml portions of dichloromethane;
(7) pre-washing with 100 ml of a dichloromethane solution of 10% triethylamine;
(8) neutralizing with 100 ml of a dichloromethane solution of 10% triethylamine;
(9) washing with three 100 ml portions of dichloromethane;
(10) adding a solution of a BOC-protected amino acid (6 mmol) dissolved in a mixture of 10 ml of DMF and 50 ml of dichloromethane;
(11) adding a 0.5M DCC/dichloromethane solution and reacting for three hours; and p1 (12) returning to the step (1) to repeat the same procedures.

The protected amino acids were added in the following order each in an amount of 6 mmol which corresponded to three equivalents of the amino group bound to the resin:

| | | |
|---|---|---|
| BOC—Lys (2-Cl-Z) | 2.5 g | 6 mmol |
| BOC—D-Leu | 1.39 g | 6 mmol |
| BOC—Lys (2-Cl—Z) | 2.5 g | 6 mmol |
| BOC—Pro | 1.29 g | 6 mmol |
| BOC—Arg (Tos) | 2.57 g | 6 mmol |
| BOC—D-Ile | 1.39 g | 6 mmol |
| BOC—Arg (Tos) | 2.57 g | 6 mmol |
| BOC—Arg (Tos) | 2.57 g | 6 mmol |
| BOC—Leu | 1.39 g | 6 mmol |
| BOC—Phe | 1.59 g | 6 mmol |
| BOC—Gly | 1.05 g | 6 mmol |
| BOC—Gly | 1.05 g | 6 mmol |
| BOC—N—Me—Tyr (2-Br—Z) | 2.78 g | 6 mmol |

After the completion of these procedures, a protected peptide having the following primary structure was synthesized on the resin; BOC-N-Me-Tyr(2-Br-Z)-Gly-Gly-Phe-Leu-Arg(Tos)-Arg(Tos)-D.Ile-Arg(Tos)-Pro-Lys(2-Cl-Z)-D.Leu-Lys(2-Cl-Z)-Trp-resin.

Then the following procedures were carried out to remove the protecting group of the peptide on the resin and to eliminate said peptide from the resin. First the protected peptide on the resin was washed with 100 ml of a dichloromethane solution containing 33% TFA, 100 ml of dichloromethane and 100 ml of methanol and dried in a desiccator overnight in vacuo. Then 9.6 g of the peptide resin was treated with 29 ml of hydrogen fluoride for one hour at 0° C. with 2.9 g of anisole. The hydrogen fluoride was distilled off and the residue was washed with absolute ether.

After being dried in vacuo, the aimed peptide was dissolved in 150 ml of a 10% acetic acid and the insoluble resin was filtered off. 850 mg of a crude peptide was obtained by lyophilization.

The crude peptide was first purified by countercurrent chromatography with BuOH:AcOH:$H_2O$ (4:1:5) system by using 250 tubes. The aimed peptide was detected in the fraction tubes Nos. 44 to 53. The yield thereof after lyophilization was 310 mg. Then ion exchange chromatography was carried out with CM-cellulose resin (column size: $\phi$2.5×25 cm). The aimed peptide was detected in the fraction tubes Nos. 78 to 87 by linear concentration gradient elution with an ammonium acetate buffer solution (0.1M to 0.5M, pH 6.5). The yield thereof after lyophilization was 115 mg. Then it was subjected to gel chromatography by using Sephadex G 25 superfine of which a column size is 1.5 cm diameter and 90 cm length, eluted with 1 n-acetic acid. The aimed peptide was detected in the fraction tube Nos. 25 to 30. The yield thereof after lyophilization was 75 mg (3.5%). The purity and structure of the resulting peptide were identified by the following methods:

(1) TLC (cellulose, Whatman Co., Ltd.)
  Detection; ninhydrin reaction
  Developing solvent A; n-BuOH:pyridine:AcOH:-$H_2O$ (15:10:3:12)
  Single spot Rf=0.78
  Developing solvent B; n-BuOH:pyridine:AcOH:$H_2O$ (42:24:4:30)
  Single spot Rf=0.68
(2) High-voltage paper electrophoresis
  Paper; Whatman 3 MM
  Detection; ninhydrin reaction
  Electrophoretic conditions; pyridine acetate buffer pH 6.4, 1500 V, 90 min, transferred to cathode in single spot Rf=1.60 (comparing with picric acid)
(3) HPLC
  Column; Nucleosil C 18, 5 μm, $\phi$4.6×250 mm
  Single peak was observed at Rt=10.5 min when eluted with 25% of acetonitrile, 75% of water and 0.065% of TFA.
(4) Amino acid analysis
  The found values from the hydrolysis with 3M mercaptoethanesulfonic acid (110° C., 24 hours) and amino acid analysis of the resulting peptide coincided with calculated values, which suggested that it was the aimed peptide.

| Amino acid | Calculated | Found |
| --- | --- | --- |
| Lys | 2 | 2.24 |
| $NH_3$ | 1 | 1.14 |
| Arg | 3 | 2.78 |
| Trp | 1 | 0.94 |
| Pro | 1 | 1.03 |
| Gly | 2 | 1.94 |
| Ile | 1 | 0.95 |
| Leu | 2 | 2.20 |
| Phe | 1 | 1.09 |

These abbreviations followed the nomenclature as stipulated by IUPAC-IUB Commission (J. Biol. Chem., 247, 977 (1972)).

OBZ1 = benzyl ester
  BOC = t-butoxycarbonyl
  2-Cl-Z = o-chlorobenzyloxycarbonyl

What is claimed is:

1. A peptide having the primary structure: N-Me-Tyr-Gly-Gly-Phe-Leu-Arg-Arg-D.Ile-Arg-Pro-Lys-D.Leu-Lys-Trp-$NH_2$ in which D.Ile and D.Leu represent a D-Ile and a D-Leu residue respectively, other abbreviations of amino acids represent each an L-amino acid residue and Me represents a methyl group.

* * * * *